(12) United States Patent
Adam (10) Patent No.: US 7,699,778 B2
(45) Date of Patent: Apr. 20, 2010

(54) ULTRASOUND CARDIAC STIMULATOR

(75) Inventor: Dan Adam, Haifa (IL)

(73) Assignee: Technion Research & Development Foundation Ltd., Haifa (IL)

(*) Notice: Subject to any disclaimer, the term of this patent is extended or adjusted under 35 U.S.C. 154(b) by 1440 days.

(21) Appl. No.: 10/505,630

(22) PCT Filed: Feb. 19, 2003

(86) PCT No.: PCT/IL03/00134

§ 371 (c)(1),
(2), (4) Date: Aug. 19, 2004

(87) PCT Pub. No.: WO03/070323

PCT Pub. Date: Aug. 28, 2003

(65) Prior Publication Data

US 2006/0052695 A1    Mar. 9, 2006

(30) Foreign Application Priority Data

Feb. 21, 2002    (IL) .................... 148299

(51) Int. Cl.
*A61B 8/00* (2006.01)
*A61B 5/00* (2006.01)

(52) U.S. Cl. .......... 600/439; 600/450; 600/459; 601/2

(58) Field of Classification Search ........ 600/424, 600/96, 437–468, 509–528; 601/1–4; 607/208, 607/301
See application file for complete search history.

(56) References Cited

U.S. PATENT DOCUMENTS

| | | | |
|---|---|---|---|
| 3,951,140 A | 4/1976 | Eggleton et al. | |
| 4,265,228 A | 5/1981 | Zoll | |
| 4,303,075 A | 12/1981 | Hellman et al. | |
| 4,549,535 A | 10/1985 | Wing | |
| 4,637,397 A | 1/1987 | Jones et al. | |
| 4,651,716 A * | 3/1987 | Forester et al. | 601/2 |
| 4,928,672 A | 5/1990 | Grasser et al. | |
| 4,974,461 A | 12/1990 | Smith et al. | |
| 5,156,154 A | 10/1992 | Valenta, Jr. et al. | |
| 5,183,040 A | 2/1993 | Nappholz et al. | |
| 5,213,098 A | 5/1993 | Bennett et al. | |
| 5,295,484 A * | 3/1994 | Marcus et al. | 600/439 |

(Continued)

FOREIGN PATENT DOCUMENTS

EP    0 504 881    9/1992

(Continued)

OTHER PUBLICATIONS

Avitall, B. et al.; "Local Effects of Electrical and Mechanical Stimulation on the Recovery Properties of Canine Ventricle;" Aug. 1982; The American Journal of Cardiology; vol. 50, No. 2; pp. 263-270.

(Continued)

*Primary Examiner*—Eric F Winakur
*Assistant Examiner*—Lawrence N Laryea (57) ABSTRACT

An ultrasound cardiac stimulation system comprising: a spatially selective ultrasound source comprising at least one ultrasound transducer located outside the circulatory system; and a controller; where the controller generates an electrical response in the heart by directing the ultrasound source to transmit a high enough power level of ultrasound to one or more locations in the heart.

75 Claims, 4 Drawing Sheets

U.S. PATENT DOCUMENTS

| | | | |
|---|---|---|---|
| 5,307,816 A * | 5/1994 | Hashimoto et al. | 600/439 |
| 5,433,731 A | 7/1995 | Hoegnelid et al. | |
| 5,635,207 A * | 6/1997 | Grinstaff et al. | 424/450 |
| 5,727,556 A | 3/1998 | Weth et al. | |
| 5,766,208 A | 6/1998 | McEwan | |
| 5,817,021 A | 10/1998 | Reichenberger | |
| 5,840,030 A | 11/1998 | Ferek-Petric et al. | |
| 5,846,200 A * | 12/1998 | Schwartz | 600/443 |
| 5,848,969 A | 12/1998 | Panescu et al. | |
| 5,935,158 A | 8/1999 | Holmstrom et al. | |
| 5,968,085 A | 10/1999 | Morris et al. | |
| 5,991,660 A | 11/1999 | Goyal | |
| 6,004,269 A | 12/1999 | Crowley et al. | |
| 6,029,518 A * | 2/2000 | Oeftering | 73/570.5 |
| 6,068,596 A | 5/2000 | Weth et al. | |
| 6,110,098 A | 8/2000 | Renirie et al. | |
| 6,141,588 A * | 10/2000 | Cox et al. | 607/9 |
| 6,152,882 A | 11/2000 | Prutchi | |
| 6,242,472 B1 * | 6/2001 | Sekins et al. | 514/396 |
| 6,330,475 B1 | 12/2001 | Renirie et al. | |
| 6,704,600 B2 * | 3/2004 | Daum | 607/30 |
| 6,719,449 B1 * | 4/2004 | Laugharn et al. | 366/127 |
| 7,429,249 B1 * | 9/2008 | Winder et al. | 601/2 |
| 2001/0031922 A1 * | 10/2001 | Weng et al. | 600/439 |
| 2002/0045810 A1 * | 4/2002 | Ben-Haim | 600/374 |
| 2002/0091339 A1 * | 7/2002 | Horzewski et al. | 601/2 |
| 2002/0165448 A1 * | 11/2002 | Ben-Haim et al. | 600/424 |
| 2002/0173784 A1 * | 11/2002 | Sliwa et al. | 606/28 |

FOREIGN PATENT DOCUMENTS

| | | |
|---|---|---|
| EP | 1480723 | 8/2003 |
| WO | WO 99/61058 | 12/1999 |
| WO | WO00/62858 | 10/2000 |
| WO | WO 00/62858 | 10/2000 |
| WO | WO 01/30397 | 5/2001 |
| WO | WO 03/070323 | 8/2003 |

OTHER PUBLICATIONS

Bagos, R. et al.; "Thresholds for Ultrasonically Induced Lung Hemorrhage in Neonatal Swine;" 1996; Ultrasound in Med. & Biol.; vol. 22, No. 1; pp. 119-128.

Carstensen, E. L. et al.; "The Search for Cavitation in Vivo;" 2000; Ultrasound in Med. & Biol.; vol. 26, No. 9; pp. 1377-1385.

Chapman, I. V. et al.; "Ultrasound-Induced Changes in Rates of Influx and Efflux of Potassium Ions in Rat Thymocytes in Vitro;" 1980; Ultrasound in Med. & Biol.; vol. 6, No. 1; pp. 47-49 and 51-58.

Dalecki, D. et al.; "A Test for Cavitation as a Mechanism for Intestinal Hemorrhage in Mice Exposed to a Piezoelectric Lithotripter;" 1996; Ultrasound in Med. & Biol.; vol. 22, No. 4; pp. 493-496.

Dalecki, D. et al.; "Age Dependence of Ultrasonically Induced Lung Hemorrhage in Mice;" 1997; Ultrasound in Med. & Biol.; vol. 23, No. 5; pp. 767-776.

Dalecki, D. et al.; "Bioeffects of Positive and Negative Acoustic Pressures in Mice Infused with Microbubbles;" 2000; Ultrasound in Med. & Biol.; vol. 26, No. 8; pp. 1327-1332.

Dalecki, D. et al.; "Effects of Pulsed Ultrasound on the Frog Heart: I. Thresholds for Changes in Cardiac Rhythm and Aortic Pressure;" 1993; Ultrasound in Med. & Biol.; vol. 19, No. 5; pp. 385-390.

Dalecki, D. et al.; "Effects of Pulsed Ultrasound on the Frog Heart: II. An Investigation of Heating as a Potential Mechanism;" 1993; Ultrasound in Med. & Biol.; vol. 19, No. 5; pp. 391-398.

Dalecki, D. et al.; "Effects of Pulsed Ultrasound on the Frog Heart: III. The Radiation Force Mechanism;" 1997; Ultrasound in Med. & Biol.; vol. 23, No. 2; pp. 275-285.

Dalecki, D. et al.; "Hemolysis In Vivo from Exposure to Pulsed Ultrasound;" 1997; Ultrasound in Med. & Biol.; vol. 23, No. 2; pp. 307-313.

Dalecki, D. et al.; "Hemorrhage in Murine Fetuses Exposed to Pulsed Ultrasound;" 1999; Ultrasound in Med. & Biol.; vol. 25, No. 7; pp. 1139-1144.

Dalecki, D. et al.; "Intestinal Hemorrhage from Exposure to Pulsed Ultrasound;" 1995; Ultrasound in Med. & Biol.; vol. 21, No. 8; pp. 1067-1072.

Dalecki, D. et al.; "Thresholds for Fetal Hemorrhages Produced by a Piezoelectric Lithotripter;" 1997; Ultrasound in Med. & Biol.; vol. 23, No. 2; pp. 287-297.

Dalecki, D. et al.; "Thresholds for Intestinal Hemorrhage in Mice Exposed to a Piezoelectric Lithotripter;" 1995; Ultrasound in Med. & Biol.; vol. 21, No. 9; pp. 1239-1246.

Dalecki, D. et al.; "Ultrasonically Induced Lung Hemorrhage in Young Swine;" 1987; Ultrasound in Med. & Biol.; vol. 23, No. 5; pp. 777-781.

Dayton, P. A. et al.; "Optical and Acoustical Dynamics of Microbubble Contrast Agents inside Neutrophils;" Mar. 2001; Biophysical Journal; vol. 90, pp. 1547-1556.

Gotoh, H. et al.; "Mechanical Stimuli Induce Intracellular Calcium Response in a Subpopulation of Cultured Rat Sensory Neurons;" 1999; Neuroscience; vol. 92, No. 4; pp. 1323-1329.

Lindner; J. R. et al.; "Microbubble Persistence in the Microcirculation During Ischemia/Reperfusion and Inflammation Is Caused by Integrin- and Complement-Mediated Adherence to Activated Leukocytes;" 2000; Circulation; vol. 101; pp. 668-675.

Lindner, J. R. et al.; "Noninvasive Imaging of Inflammation by Ultrasound Detection of Phagocytosed Microbubbles;" 2000; ; Circulation; vol. 102; pp. 531-538.

Lindner, J. R. et al.; "Noninvasive Ultrasound Imaging of Inflammation Using Microbubbles Targeted to Activated Leukocytes;" 2000; ; Circulation; vol. 102; pp. 2745-2750.

MacRobbie, A. G. et al.; "Thresholds for Premature Contractions in Murine Hearts Exposed to Pulsed Utrasound;" 1997; Ultrasound in Med. & Biol.; vol. 23, No. 5; pp. 761-765.

Montalibet, A. et al.; "Electric Current Generated by Ultrasonically Induced Lorentz Force in Biological Media;" 2001; Medical & Biological Engineering & Computing; vol. 39; pp. 15-20.

Raeman, C. H. et al.; "Exposure-Time Dependence of the Threshold for Ultrasonically Induced Murine Lung Hemorrhage;" 1996; Ultrasound in Med. & Biol.; vol. 22, No. 1; pp. 139-141.

Skyba, D. M. et al.; "Direct In Vivo Visualization of Intravascular Destruction of Microbubbles by Ultrasound and its Local Effects on Tissue;" 1998; Circulation; vol. 98; pp. 290-293.

Wan, X. et al.; "Activation of Mechanosensitive Currents in Traumatized Membrane;" 1999; Am. J. Physiol.; vol. 276 (Cell Physiol. 45); pp. C318-C327.

Zhong, P. et al.; "Dynamics of Bubble Oscillation in Constrained Media and Mechanisms of Vessel Rupture in SWL;" 2001; Ultrasound in Med. & Biol.; vol. 27, No. 1; pp. 119-134.

Communication Pursuant to Article 94(3) EPC Dated Jun. 12, 2009 From the European Patent Office Re.: Application No. 03706886.3.

* cited by examiner

ULTRASOUND CARDIAC STIMULATOR

RELATED APPLICATIONS

The present application is a U.S. national application of PCT Application No. PCT/IL03/00134, filed on Feb. 19, 2003.

FIELD OF THE INVENTION

The present invention is related to the field of cardiac diagnosis and therapy.

BACKGROUND OF THE INVENTION

The myocardium is susceptible to mechanical stimulation: case reports have detailed incidents of cardiac arrest due to a ball or a fist hitting the person's thorax. Physiological studies have reported initiation of an action potential due to a mechanical stimulation such as tapping of the epicardium [Avitall, B., Levine, H. J., Naimi, S., Donahue, R. P., Pauker, S. G., and Adam, D. R., "Local effects of electrical and mechanical stimulation on the recovery properties of canine ventricle," *Am. J. Cardiology* 50, 263-270 (1982)], or due to stretch. Separately, high energy ultrasound pulses have been reported to shatter kidney stones, while also affecting inner cellular structures and membrane properties. In particular, it has been reported that ultrasound pulses increase membrane permeability and specific ion flow. Ultrasound transducers attached to cardiac catheters have been used to induce electrical activity locally in the heart, for diagnostic purposes. External ultrasound transducers used for imaging have also been observed to induce action potentials in the heart, inadvertently, especially when contrast agents containing small bubbles are injected into the bloodstream. Because of the danger of inducing action potentials in the heart in an uncontrolled way, great care is taken during ultrasound imaging of the heart not to induce action potentials.

Direct electrical stimulation of the heart is done for cardiac pacing, usually via electrodes implanted during surgery. Electrical stimulation is also used to measure cardiac response, as a diagnostic, and for this purpose electrodes may be inserted by catheters via the venous or arterial system. Catheters are also used to carry laser or RF or ultrasound energy to specific sites in the heart or elsewhere in the circulatory system, in order to ablate tissue for therapeutic purposes. All of these invasive procedures involve obvious risks and expenses.

Ultrasound energy from external transducer arrays has been focused on tumors in order to destroy them by heating.

SUMMARY OF INVENTION

An aspect of some embodiments of the invention relates to stimulating cardiac tissue, or any other excitable tissue such as muscles and nerves, using ultrasound, for diagnostic and/or therapeutic purposes, using transducers located outside the body, or in the esophagus or other non-invasive body channels, such as the nasal cavities. Optionally, ultrasound contrast agents, for example microbubbles or liposomes, are used to enhance the procedure, for example by increasing the sensitivity of the cardiac tissue to stimulation.

In some embodiments of the invention, an imaging system is used to track and observe the heart before, during, and/or after the cardiac tissue is stimulated. This is done, for example, in order to observe the local or global mechanical response of the heart to the stimulation, or to focus the ultrasound energy on the correct spot. Optionally, the imaging system is an ultrasound imaging system, using the same transducers as are used for stimulation. Alternatively or additionally, other ultrasound transducers may be used for imaging. Alternatively or additionally, a Computer Aided Tomography system using x-rays, a Magnetic Resonance Imaging system, or any imaging system known to the art may be used. Optionally, contrast agents are used to improve image quality, and/or to distinguish between perfused and non-perfused tissue.

In some embodiments of the invention, the location and orientation of the heart, or a particular point on the heart, are tracked in real time while ultrasound is used to stimulate the heart. Such tracking makes it possible to repeatedly focus ultrasound on the same spot in the heart, or to successively focus ultrasound on two or more spots with known relative positions.

In some embodiments of the invention, ultrasound waves are focused on one small spot in the heart, to stimulate the tissue, and the response to stimulation is observed. This stimulation spot can be deep inside the myocardium, as well as on the exterior or interior surface of the heart. Optionally, after a period of time, the ultrasound waves are focused on a different stimulation spot. Alternatively or additionally, the ultrasound waves are focused on more than one stimulation spot simultaneously, or nearly simultaneously relative to the speed of propagation of signals in the heart. For each stimulation spot or set of stimulation spots, measurements are optionally made of the intensity and duration of ultrasound needed to induce action potentials, either propagating or non-propagating, and the spatial distribution of the potential is optionally measured, as a function of time. The mechanical response of tissue to action potentials is optionally measured as a function of time, for example by observing changes in thickness and motion of the cardiac wall, at the stimulation spot and at other spots.

In an exemplary embodiment of the invention, the following configuration is used. The ultrasound source is aimed at a particular location in the heart and its firing is synchronized to the cardiac cycle, for example, using an ECG (which may provide local electrical information) or using an analysis of a series of images. The analysis may be automatic or manual, for example. The imager is also aimed at the particular location and/or at a location where an effect of the excitation is expected and/or is desired to be studied. Optionally, the imager is closely synchronized with the stimulating ultrasound, which may make it easier to detect the short-term mechanical response of the heart tissue to the ultrasound. It may also be possible to detect the motion of the heart wall due to the pressure of the ultrasound. In operation, the imager can detect the exact location of excitation (even if the aiming is not precise), for example, by detecting non-linear effects at the location. In addition, the imager can capture a development of mechanical response to the excitation, over a period of time, due to the action potential. Further, this detected response may be synchronized with a measurement of electrical activity from outside the body (e.g., using a high resolution ECG) or from inside the body (e.g., using a catheter). It should be noted that in this manner a map having a resolution better than the aiming ability can be created, by marking the map with the actual excitation signal location. In any case, the analysis of the detected response and the ECG may be manual or automatic. For example, the mechanical response to the action potential is found automatically by using image analysis software to measure changes in wall thickness. When this measurement is synchronized to a local ECG, a delay in mechanical response is calculated.

The results of these measurements are optionally used for identifying ischemic tissue that is permanently damaged, and distinguishing it from tissue that is stunned or hibernating but could be revived. Tissue that is overly sensitive to stimulation, and could give rise to arrhythmias, may also be identified. Maps of the location of healthy and pathological tissue in the heart are used in some embodiments of the invention to design spatial and temporal sequences of stimulation that are optimal for pacemaking. Optionally, such sequences are tested and compared using ultrasound stimulation. Optionally, some tissue is ablated by ultrasound, or by other means as known in the art.

In some embodiments of the invention, ultrasound is used to increase membrane permeability at particular locations in the heart and/or particular times in the cardiac cycle, in order to selectively increase the absorption or effect of drugs at those locations and/or times. Optionally, the drugs are delivered to specific locations by a cardiac catheter.

In some embodiments of the invention, a phased array of transducers is used to generate the focused ultrasound pulses. Alternatively or additionally, a single transducer with focusing is used. Optionally, the transducers are placed on the outside of the chest. To avoid having the ultrasound energy blocked by the ribs, the transducers optionally are placed between the ribs. Additionally or alternatively, the transducers are placed on the sternum, or below the rib cage. Additionally or alternatively, the transducers are placed non-invasively inside the body, for example in the esophagus.

In some embodiments of the invention, ultrasound pulses are used to provide temporary pacing of the heart, for example when a conventional pacemaker is temporarily not operating, or during bradycardia. Optionally, different temporal and spatial sequences of ultrasound pulses are tested and compared, in order to find the best sequence to use for pacing. The different sequences are evaluated using, for example, electrocardiograph data, systolic pressure measurements, and/or images showing the mechanical response of the heart, including systolic and diastolic left ventricular volume and ejection fraction.

In some embodiments of the invention, a cardiac catheter is used to provide direct electrical simulation of the heart, in addition to the stimulation by ultrasound. Direct electrical stimulation may help to identify tissue pathologies by comparing its effects to the effects of mechanical stimulation by ultrasound. In one example, such a comparison is used to distinguish stunned from hibernating myocardium. In another example, the ultrasound pulses are focused at a coarse resolution, and used to produce a coarse map of pathological tissue, and a cardiac catheter is used to map certain regions more precisely. The imaging system is optionally used to determine the precise location of the cardiac catheter. In addition to or instead of electrically stimulating the heart, the catheter optionally is used to ablate or otherwise kill cardiac tissue, optionally monitoring the process with the imaging system. This killing is done by any means known to the art. For example the catheter brings electric power to an ohmic or inductive heating element, a refrigerating element, an ultrasound transducer or a radio frequency transmitter in the circulatory system, or the catheter carries laser light on a fiber optic cable, or carries a drug.

There is thus provided, in accordance with an embodiment of the invention, an ultrasound cardiac stimulation system comprising:

a spatially selective ultrasound source comprising at least one ultrasound transducer located outside the circulatory system; and a controller;

wherein the controller generates an electrical response in the heart by directing the ultrasound source to transmit a high enough power level of ultrasound to one or more locations in the heart.

Optionally, there is an injector which injects cardiac drugs into the bloodstream, and the controller changes the rate at which cardiac tissue absorbs the drugs by directing the ultrasound source to transmit a high enough power level of ultrasound to one or more locations in the heart.

Optionally, the controller is operative to choose the ultrasound power level.

In an embodiment of the invention, the system has sufficient precision to control the ultrasound power level supplied to cardiac tissue to within ±20%.

Optionally, the system has sufficient precision to control the ultrasound power level supplied to cardiac tissue to within ±10%.

Optionally, the system has sufficient precision to control the ultrasound power level supplied to cardiac tissue to within ±3%.

In an embodiment of the invention, an injector which injects one or both of drugs for treating the heart and contrast agents into the bloodstream.

Optionally, the controller is operative to reduce the power level of ultrasound when the contrast agents are injected.

In an embodiment of the invention, the controller is operative to choose the one or more locations to which the ultrasound is transmitted.

Optionally, the controller controls the ultrasound source to direct ultrasound energy to a designated location, and the point of highest power flux density falls within an axial precision of 3 mm of said designated location.

Alternatively, the axial precision is 1.5 mm.

Optionally, the point of highest power flux density remains within the axial precision of the designated location for at least 1 millisecond.

Optionally, the point of highest power flux density remains within the axial precision of the designated location for at least 10 milliseconds.

Optionally, the controller controls the ultrasound source to direct ultrasound energy to a designated location, and the point of highest power flux density falls within a transverse precision of 1 mm of said designated location.

Alternatively, the transverse precision is 0.5 mm.

Optionally, the point of highest power flux density remains within the transverse precision of the designated location for at least 1 millisecond.

Optionally, the point of highest power flux density remains within the transverse precision of the designated location for at least 10 milliseconds.

In an embodiment of the invention, the controller controls the ultrasound source to direct a high enough power level of ultrasound to one or more locations in the heart to kill cardiac tissue by heating it.

Alternatively or additionally, the controller controls the ultrasound source to direct a high enough power level of ultrasound to one or more locations in the heart to kill cardiac tissue by cavitation.

In an embodiment of the invention, there is an electrocardiograph which measures the timing of the cardiac cycle.

Optionally, the electrocardiograph is operative to distinguish the electrical response to the ultrasound, originating in any one chamber of the heart, from the electrical response originating in any other chamber of the heart.

Optionally, the electrocardiograph is operative to distinguish the electrical response to the ultrasound, originating in one side of any chamber of the heart, from the electrical response originating in the other side of said chamber of the heart.

Optionally, the electrocardiograph is operative to distinguish the electrical response to the ultrasound, originating at any location in the heart, from the electrical response originating one centimeter away from said location.

Optionally, the electrocardiograph is operative to distinguish the electrical response to the ultrasound, originating at any location in the heart, from the electrical response originating one millimeter away from said location.

Optionally, the system uses feedback from the electrocardiograph to control the ultrasound power level.

In an embodiment of the invention, the controller is operative to make a map of the heart, showing the ultrasound power flux required to generate the electrical response at each of several locations in the heart.

Optionally, the controller is operative to direct the ultrasound source to transmit a first sequence of timed localized pulses of ultrasound energy to the heart, and a second such sequence which differs from the first sequence in one or both of timing and location of the pulses, and the controller is operative to collect a first data set showing the effects of the first sequence on the heart, and a second data set showing the effects of the second sequence on the heart.

Optionally, the first data set and the second data set comprise data from the electrocardiogram.

Optionally, there is a memory which is operative to store the first data set and the second data set, a data analyzer which is operative to analyze data and produce analysis results from the first data set and the second data set, and a display which displays the analysis results.

Optionally, the first data set and the second data set comprise data on systolic pressure.

Optionally, the first sequence and the second sequence differ in timing of the pulses.

Alternatively or additionally, the first sequence and the second sequence differ in location of the pulses.

In an embodiment of the invention, there is a cardiac imaging system which produces images showing the position of one or more locations on the heart.

Optionally, the first data set and the second data set comprise data from the cardiac imaging system.

Optionally, there is an image analyzer which analyzes images produced by the cardiac imaging system for the first sequence and the second sequence, and calculates one or more of the systolic left ventricular volume for the first and second sequence, the diastolic left ventricular volume for the first and second sequence, and the ejection fraction for the first and second sequence.

Optionally, the images produced by the imaging system show the mechanical response of the heart to stimulation produced by the ultrasound.

Optionally, the imaging system is in a fixed position and orientation with respect to the ultrasound source.

Alternatively or additionally, there are sensors which determine the relative position and orientation of the imaging system and the ultrasound source.

Alternatively or additionally, the imaging system determines the relative position and orientation of the ultrasound source by imaging it.

Optionally, the controller coordinates the timing of the imaging system with the timing of the ultrasound source.

Optionally, the controller is operative to make a map of the heart, using data from the imaging system, showing the mechanical response of the heart at one or more locations to ultrasound energy transmitted to one or more locations.

Optionally, the system uses feedback from the imaging system to control the ultrasound power level.

Optionally, the imaging system uses ultrasound imaging.

Optionally, the imaging system shares one or more ultrasound transducers with the ultrasound source used to generate the electric response in the heart.

Alternatively, the imaging system does not share any ultrasound transducers with the ultrasound source used to generate the electric response in the heart.

Alternatively or additionally, the imaging system comprises a computerized tomography x-ray imaging system.

Alternatively or additionally, the imaging system comprises a magnetic resonance imaging system.

Optionally, there is image processing software which analyzes the images to determine the position of one or more locations on the heart.

Optionally, the image processing software determines the position of one or more locations on the heart in real time during a cardiac cycle.

Optionally, the controller coordinates the timing of the transmission of ultrasound with the cardiac cycle.

In an embodiment of the invention, there is a cardiac catheter which generates an electrical response in the heart, and a calibration mode of the controller, wherein the controller, when it is in the calibration mode, calibrates the ultrasound power transmitted to the heart by the ultrasound array, by comparing a physiological response induced by the ultrasound array to a physiological response induced by the catheter.

Optionally, the physiological responses compared by the controller comprise electrical responses.

Alternatively or additionally, the physiological responses compared by the controller comprise mechanical responses.

Optionally, the cardiac catheter generates an electrical response by direct electric stimulation.

Alternatively or additionally, the cardiac catheter comprises an internal ultrasound transducer, and the cardiac catheter generates an electrical response by transmitting ultrasound.

In an embodiment of the invention, the cardiac catheter kills cardiac tissue.

Optionally, the cardiac catheter comprises a light guide, and the light guide carries light from the laser, which light kills cardiac tissue.

Optionally, the ultrasound source comprises a phased array of the ultrasound transducers.

Optionally, at least one of the at least one ultrasound transducers is adapted for use on the surface of the body.

Optionally, the at least one ultrasound transducers comprise at least two ultrasound transducers, sized and spaced so that they can be placed between the ribs, in such a way as to avoid blocking of ultrasound by the ribs.

Alternatively or additionally, at least one of the at least one ultrasound transducers is adapted for use in the esophagus.

Alternatively or additionally, at least one of the at least one ultrasound transducers is adapted for use in a nasal cavity.

Optionally, the ultrasound source and the controller are operative to direct the ultrasound energy with 90% of the power flux falling within 3 mm transversely of the point of highest power flux density.

Alternatively or additionally, the ultrasound source and the controller are operative to direct the ultrasound energy with 90% of the power flux falling within 1.5 mm transversely of the point of highest power flux density.

Alternatively or additionally, the ultrasound source and the controller are operative to direct the ultrasound energy with 90% of the power flux falling within 1 mm transversely of the point of highest power flux density.

Optionally, the ultrasound source and the controller are operative to direct the ultrasound energy with the power flux spreading out to 50% of its highest density within 6 mm axially of the point of highest power flux density.

Alternatively or additionally, the ultrasound source and the controller are operative to direct the ultrasound energy with the power flux spreading out to 50% of its highest density within 3 mm axially of the point of highest power flux density.

Alternatively or additionally, the ultrasound source and the controller are operative to direct the ultrasound energy with the power flux spreading out to 50% of its highest density within 1.5 mm axially of the point of highest power flux density.

Optionally, the ultrasound source and the controller are operative to direct the ultrasound energy with a power flux density greater than 30 watts per square centimeter at the point of highest power flux density.

Alternatively or additionally, the ultrasound source and the controller are operative to direct the ultrasound energy with a power flux density greater than 100 watts per square centimeter at the point of highest power flux density.

Alternatively or additionally, the ultrasound source and the controller are operative to direct the ultrasound energy with a power flux density greater than 300 watts per square centimeter at the point of highest power flux density.

Optionally, the ultrasound source and the controller are operative to direct the ultrasound energy in a pulse lasting less than 10 milliseconds.

Alternatively or additionally, the ultrasound source and the controller are operative to direct the ultrasound energy in a pulse lasting less than 1 millisecond.

Optionally, the ultrasound source and the controller are operative to direct the ultrasound energy in a pulse lasting for a duration within 10% of a duration for which the controller is directed to direct the energy.

Optionally, the ultrasound source and the controller are operative to direct the ultrasound energy at a frequency greater than 0.5 megahertz and less than 6 megahertz.

There is thus also provided a method of changing a cardiac stimulation sequence for a patient, comprising:
a) choosing a test sequence of locations in the heart of the patient, and a time in the cardiac cycle to stimulate each location;
b) stimulating the test sequence of locations at the chosen times in the cardiac cycle, using an ultrasound cardiac stimulation system from outside the heart;
c) evaluating a change in cardiac synchronization of the patient associated with the test sequence;
d) choosing a stimulation sequence for a pacemaker, based at least partly on the change in cardiac synchronization that the test sequence produces; and
e) changing a stimulation sequence of the heart to conform to the chosen stimulation sequence.

In an embodiment of the invention, using an ultrasound cardiac stimulation system from outside the heart comprises using an ultrasound stimulation system from outside the body.

Optionally, changing a stimulation sequence of the heart comprises installing a pacemaker.

Alternatively or additionally, changing a stimulation sequence of the heart comprises adjusting a pacemaker.

Optionally, adjusting a pacemaker comprises programming a pacemaker.

Optionally, adjusting a pacemaker comprises adjusting a pacemaker to obtain improved cardiac synchronization.

In an embodiment of the invention, (a), (b) and (c) are performed a plurality of times for different test sequences, and choosing an optimal stimulation sequence is based at least partly on the change in a measure of cardiac performance that the different test sequences produce.

Optionally, the measure of cardiac performance comprises cardiac output.

Optionally, evaluating the change in the measure of cardiac performance comprises using systolic pressure measurements.

Alternatively or additionally, evaluating the change in the measure of cardiac performance comprises using images of a mechanical response of the heart to the stimulation.

Optionally, at least one of the test sequences comprises a plurality of locations with the same chosen time.

Optionally, evaluating the change in cardiac synchronization comprises using electrocardiograph data.

BRIEF DESCRIPTION OF THE DRAWINGS

Exemplary embodiments of the invention are described in the following sections with respect to the drawings. The drawings are generally not to scale. The same or similar reference numbers are used for the same or related features on different drawings. Features found in one embodiment can also be used in other embodiments, even though all features are not shown in all drawings.

DETAILED DESCRIPTION OF EXEMPLARY EMBODIMENTS

Figure 1:
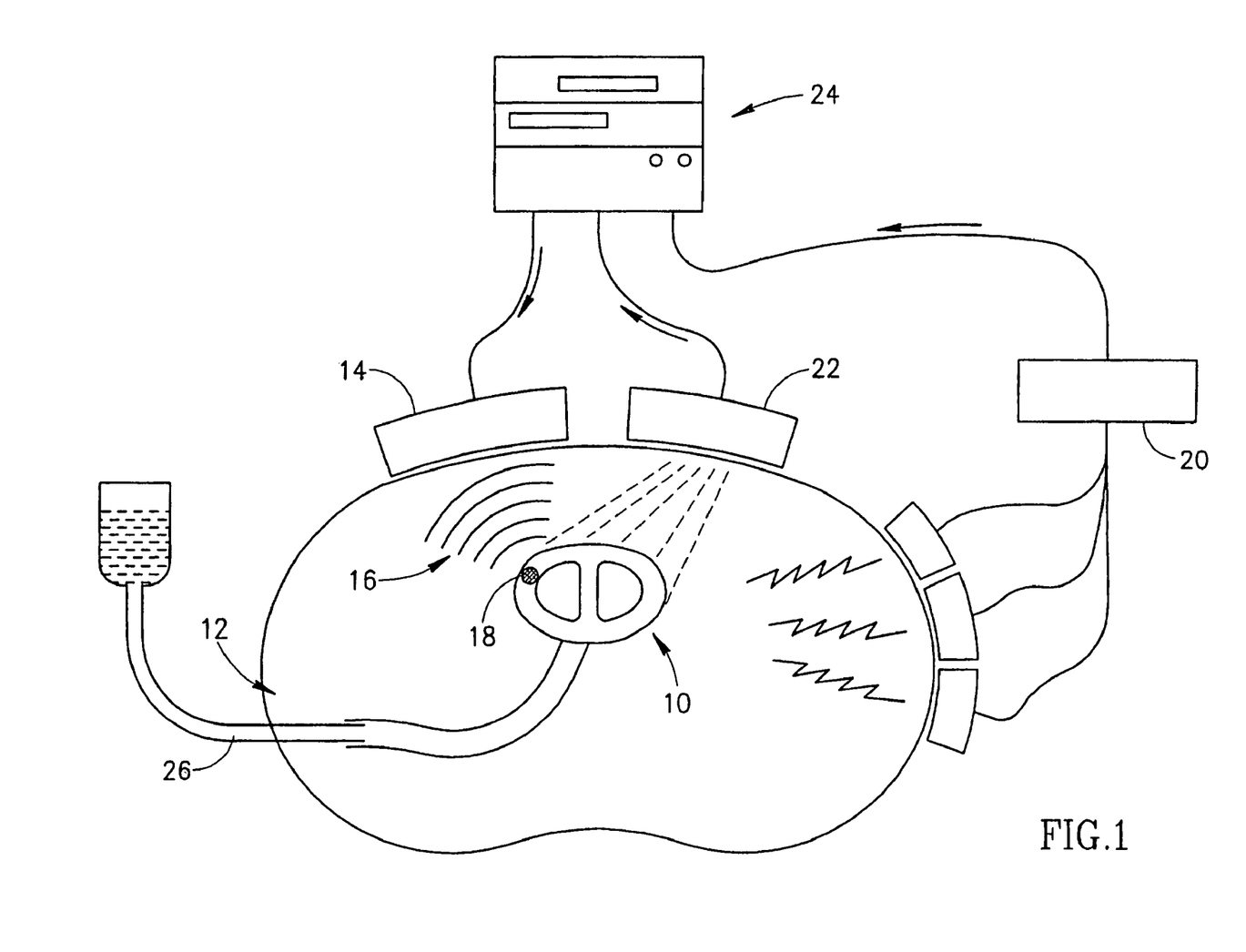
FIG. 1 is a schematic cross-sectional view of the chest and heart, showing ultrasound systems used for stimulating the heart, according to an exemplary embodiment of the invention.

FIG. 1 schematically shows an ultrasound system according to an exemplary embodiment of the invention. A heart 10 is shown in a cross-section of a patient's chest 12. A phased array 14 of ultrasound transducers focuses ultrasound waves 16 on a spot 18 in the wall of the heart, stimulating cardiac tissue at that spot and possibly inducing action potentials, detected by an electrocardiograph 20. By adjusting the relative phases and amplitudes of the different transducers in the array, the ultrasound can generally be focused on any desired spot 18. Alternatively, any other method of focusing ultrasound known to the art is used to focus the ultrasound waves on spot 18. The diameter of the spot cannot be much smaller than one wavelength, assuming that it is in the far field of the transducers, i.e. at least several wavelengths away from the transducers. If it is desired to focus the ultrasound on a region much smaller than the thickness of the myocardium, the frequency of the ultrasound optionally has a frequency approximately 1 MHz or higher, which would have a wavelength in the body of about 1.5 mm or less. Ultrasound transducers exist which can operate at frequencies as high as 10 MHz. If the frequency is too high, however, and the desired focused spot is not close enough to the transducers, then the ultrasound will be largely absorbed before reaching the desired spot, and higher transducer power or more transducers will be needed to produce the same ultrasound power flux at the spot. Typically, frequencies between 0.5 and 6 MHz are used, and the focused spot is elliptical, 1 to 2 mm in diameter and 4 to 6 mm in length in the direction of propagation, with the acoustic pressure outside the spot significantly lower than the peak pressure. Focused spots with dimensions greater or smaller than these values, for example 0.5 mm to 4 mm in diameter and 2 mm to 10 mm in length, are also optionally used. Peak acoustic pressures are typically 2 to 4 MPa, corresponding to powers of 125 to 500 watts per square centimeter, and pulse lengths are typically 1 to 10 milliseconds long. However, optionally ultrasound pulses with frequencies, powers and pulse lengths of 1 to 5 MPa, corresponding to 30 to 800 watts per square centimeter, or even greater than or less than this range, are used.

Transducer array 14 is shown outside the chest in FIG. 1. To avoid the problem of ultrasound waves reflecting from the ribs, which have a very different acoustic impedance than the soft parts of the body, the transducers are optionally placed between the ribs, or below the rib cage. Alternatively, they are placed inside the chest, in the esophagus.

An imaging system 22 is used to determine the position and orientation of the heart, relative to transducer array 14, so that ultrasound energy can be accurately focused on a desired spot on the heart by transducer array 14. Although FIG. 1 shows an imaging system that is separate from transducer array 14, optionally transducer array 14 is used for an ultrasound imaging system, as well as for stimulating cardiac tissue. In this case, ultrasound waves for imaging purposes are optionally transmitted alternately with ultrasound waves for cardiac stimulation. If the imaging waves and stimulating waves are transmitted close enough together in time, then the heart will not move very much, and the information from the imaging system can still be used to accurately focus the stimulating waves. Alternatively or additionally, the stimulating waves themselves are used for imaging. The imaging system need not be an ultrasound imaging system. It could be an x-ray CAT system, or an MRI system, or any other medical imaging system known to the art.

If imaging system 22 is not an ultrasound imaging system using the same transducer array 14 that is used for stimulation, then it may be desirable to know the relative position and orientation of imaging system 22 and transducer array 14. Ultrasound can then be used to stimulate a spot whose position is defined by imaging system 22, and imaging system 22 can image a spot that has been stimulated, observing the effects of the stimulation. Optionally, transducer array 14 is rigidly connected to imaging system 22, so that they always have the same relative position and orientation. Alternatively, there are sensors mounted on transducer array 14, imaging system 22, or both of them, which sense the relative position and orientation of transducer array 14 and imaging system 22. Alternatively, imaging system 22 determines the relative position and orientation of transducer array 14 by imagining it. This option is especially useful when transducer array 14 is in the esophagus.

A computer 24 controls the phase, amplitude, and timing of ultrasound waves emitted by the transducers in transducer array 12, using input from the human operator, the imaging system, and the electrocardiograph. Details of how this is done, according to an embodiment of the invention, are given in FIG. 2. Computer 24 could comprise an general purpose computer running appropriate software, or custom-designed control circuitry, or a combination of the two.

FIG. 1 schematically shows an intravenous tube 26, which is used to introduce contrast agents into the bloodstream, during ultrasound stimulation. Contrast agents, which are encapsulated small gas bubbles, significantly attenuate the propagating ultrasound energy, reflecting, scattering and absorbing it. The contrast agent bubbles oscillate and sometimes burst, producing extremely high pressures locally. This enhances the stimulating effect of ultrasound on cardiac tissue. As a result, lower power transducers can be used to produce the same stimulation effect, and there may be less heating of tissue for the same stimulation effect. Contrast agents are also useful in imaging, for example for showing the precise boundaries of tissue with normal perfusion of blood and regions with reduced or no perfusion.

Alternatively or additionally, intravenous tube 26 is used to introduce drugs into the bloodstream during ultrasound stimulation of the heart. Since ultrasound stimulation can increase the permeability of cell membranes, certain locations in the heart will be induced to take up drugs from the bloodstream, more than other regions that are not stimulated. The uptake of drugs can also be timed to occur at certain times in the cardiac cycle, if the ultrasound stimulation is gated with an electrocardiograph. Alternatively or additionally, the contrast agents and/or the drugs can be introduced into the heart by a cardiac catheter, rather than intravenously, allowing additional control over the spatial and temporal distribution of the contrast agents and/or drugs.

Figure 2:
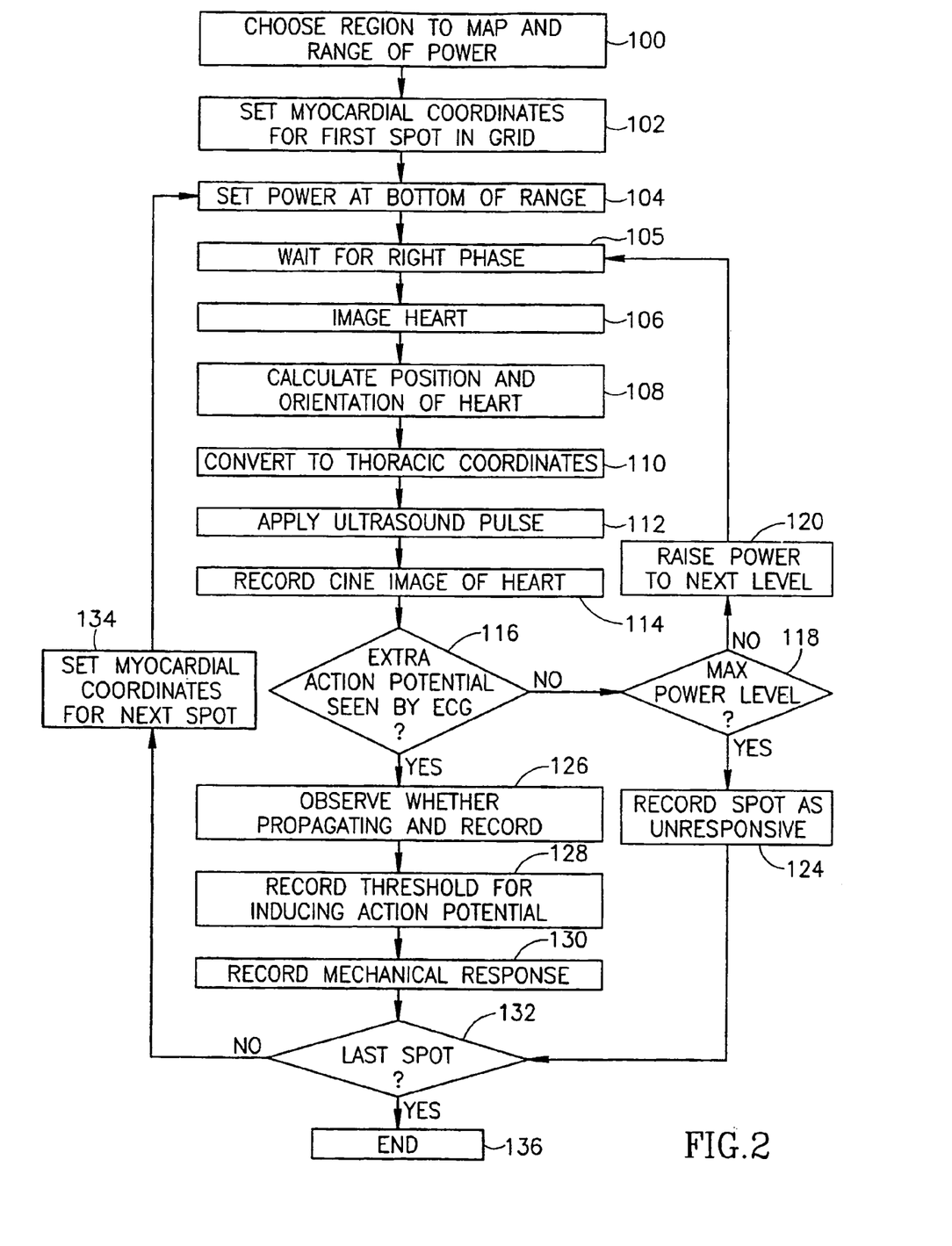
FIG. 2 is a flowchart illustrating how a map is made of the sensitivity of the heart to stimulation by ultrasound pulses.

FIG. 2 is a flowchart showing how the transducer array is used to map regions of healthy and pathological tissue in the heart, according to an exemplary embodiment of the invention. Tissue is optionally classified as healthy or pathological according to one or more of several criteria, for example:

Ultrasound power level required to induce an action potential

Time delay after ultrasound energy is applied, before action potential appears

Refractory period after action potential is induced, before another action potential can be induced Magnitude and delay of mechanical response to action potential Amplitude and duration of action potential The flowchart in FIG. 2 illustrates only how the first criterion, ultrasound power level required to induce an action potential, is mapped, but optionally any one or combination of these criteria are used to make a map. Using only the first criterion, the map identifies regions which are more susceptible than normal, or less susceptible than normal, to producing extra action potentials (beyond those associated with the regular heartbeat) when stimulated by ultrasound. Such a map can reveal the location of ischemic tissue, which typically requires higher than normal ultrasound levels to produce an action potential, and/or tissue which is susceptible to arrhythmias, which may require a lower than normal ultrasound level to produce an action potential.

The steps shown in the flowchart in FIG. 2 are optionally performed by a controller, for example a computer with an interface to the human operator. At 100, the initial step in the flowchart, a region is chosen for mapping, either the whole heart or a part of the heart, and the range of ultrasound power levels is optionally chosen. This range starts at a level well below the power that would be needed to induce an action potential in normal tissue, and ends at a level above the power that would be needed to induce an action potential in normal tissue, but optionally not at such a high level that the tissue could be damaged by heating or cavitation. The region for mapping is optionally chosen by the operator as a range of myocardial coordinates, defined in relation to the heart tissue, i.e. a given point on the heart has constant myocardial coordinates even while its absolute position is changing because the heart is beating. Alternatively, the range could be chosen by the operator by dragging a mouse across a 3-D displayed image of the heart (for example, a series of 2-D cross-sections) frozen at a particular phase in the cardiac cycle. Optionally, in addition to choosing a range of positions and powers, a phase in the cardiac cycle, or a set of phases, is also chosen for mapping. The response of tissue to stimulation generally depends on the phase in the cardiac cycle at which the stimulation is applied. Optionally, instead of setting the range of positions, powers, and phase initially, they are chosen or changed during the procedure.

In 102 and 104, the myocardial coordinates of the spot to be stimulated are set at the first point on the grid to be mapped, and the power is set at the bottom of the range. In 105, the controller waits for the desired phase in the cardiac cycle, using electrocardiograph data, for example, to determine at what time the desired phase occurs. In 106, a quick image, which need not have high resolution, is made of the heart, in order to locate the absolute position (relative to the transducers) of the spot to be stimulated. Making an error in location of the focused spot is potentially dangerous, since a high power ultrasound pulse intended for an insensitive spot could be focused by mistake on a very sensitive area and induce fibrillation. In 108 and 110, the image made in 106 is used to determine the orientation and location of the heart, and this information is used to convert the myocardial coordinates of the point being stimulated to thoracic coordinates, defined relative to the chest cavity (and hence to the transducers, which are optionally pressed against the outside of the chest). Some details of how this calculation is done are given below in the description of FIG. 3. If the imaging and calculation could be done in less than 50 milliseconds, or better yet in less than 10 milliseconds, then the heart would move very little between the time it is imaged and the time the ultrasound energy is applied for stimulation. Alternatively, instead of performing 106, 108 and 110, the range of points to be mapped is directly defined in terms of thoracic coordinates at a particular phase in the cardiac cycle, and the ultrasound energy is always applied at the same phase in the cycle. A disadvantage of this alternative method is that there could be variations in position and orientation of the heart from one heartbeat to the next.

If the ultrasound transducers are located in the esophagus rather than on the outside of the chest, then it may not be sufficient just to define the position of the point to be mapped in thoracic coordinates. In addition, it may be necessary to take into account changes in position of the transducers relative to the chest cavity. Optionally this is done by using an external imaging system to locate the position of the stimulating transducers in the esophagus. Alternatively, if the same transducers are used for stimulation and imaging, then those transducers can be used directly to find the location of the heart (or of the desired point on the heart) relative to the transducers.

In 112, the stimulating ultrasound energy is focused on the desired spot on the heart. As described above in the description of FIG. 1, this is optionally done by first using a computer to calculate the phases and amplitudes of the transducers in the array, needed to focus ultrasound energy on the desired spot. In 114, a cine (moving) image is optionally made of the heart, in order to assess the mechanical response of the heart, if any, to the stimulation. Optionally, instead of storing the entire cine image, the image is processed to track only a limited set of points on the heart, sufficient to characterize the mechanical response of the heart, and only these results are stored. If the imaging system does not use the transducers used for stimulation, then the cine imaging optionally begins before the stimulation is applied, and continues while the stimulation is applied and for a given period afterwards. Even if the same transducers are used for imaging and stimulation, the cine imaging optionally begins before the stimulation, and is briefly interrupted while the transducers are used for stimulation, and resumed afterwards. Optionally the cine image or a still image is precisely synchronized with the ultrasound stimulation, and is used to detect the short-term mechanical response of the heart tissue to the ultrasound stimulation, which may provide more information about the exact location of the ultrasound stimulation.

At 116, the controller examines data, for example from an electrocardiograph, to determine whether the ultrasound stimulation induced an action potential, beyond the action potential that already existed as part of the natural cardiac cycle. The electrocardiograph provides some information about the spatial distribution of action potentials, as well as their amplitude and time dependence. Optionally, the electrocardiograph is calibrated before it is used to measure induced action potentials, for example by comparing the induced action potentials to the regular action potential. If no extra action potential is observed, and if the power level is not yet at the top of the chosen range (118), then the power is raised to the next level (120), and the flow goes back to 105, in preparation for a new application of ultrasound energy at the same spot. If the power was already at the maximum level, then this spot is recorded as unresponsive (124), and the flow goes to 132.

Optionally, instead of starting at the lowest power level and increasing the power one step at a time, the power starts at the middle of the range, at a level that has a 50% chance of exciting an action potential, according to some model. If an action potential is seen, then the power is lowered to a level that now has a 50% chance of eliciting an action potential, taking into account the previous results. If an action potential is not seen, then the power is raised to a level that now has a 50% chance of eliciting an action potential, taking into account the previous results. This procedure is continued until the exact threshold for eliciting an action potential is found, to the desired precision. This "zeroing in" procedure has an advantage over the "one step at a time" procedure, in that the number of steps required scales as the logarithm of the desired precision, rather than scaling linearly with the desired precision. A disadvantage of the "zeroing in" procedure is that it might overstimulate a very sensitive spot, causing fibrillation. Many other procedures are possible for determining the threshold for eliciting action potentials, which will be apparent to persons skilled in the art.

If an extra action potential was seen, then the data is examined to see whether the action potential is propagating, and how it propagates (126). This information is recorded (128), and (130) any mechanical response is assessed (based on the cine image made in 114, for example), and recorded. Optionally, image processing software is used to assign one or more quantitative values to characterize the mechanical response. Alternatively or additionally, the mechanical response could be characterized by the operator after viewing the cine image. Alternatively or additionally, the cine image for each spot is stored, and the mechanical response is evaluated at leisure after the map of action potential threshold is completed.

At 132, if all spots in the grid have not been examined, then (134) the myocardial coordinates are set for the next spot in the grid, and the flow goes back to 104. Once all spots in the grid have been examined, the procedure ends (136). The recorded data on the ultrasound power threshold needed to induce an action potential at each point, and on the propagation of induced action potentials, are then used to create one or more maps, for example using post-processing software.

The maps could show the propagation paths, as well as the action potential threshold at each spot. The accuracy of the map showing action potential thresholds will be confirmed if it is consistent with the map of propagation paths, for example if it shows that regions that are resistant to inducing action potentials are also regions that block propagation of action potentials induced elsewhere.

Although the flowchart in FIG. 2 assumes that ultrasound stimulation is only applied at one phase in the cardiac cycle, optionally a map could be made for each of several phases. For example, instead of ending the procedure at 136, the controller could change the phase and loop back to 102, until all desired phases were examined. Alternatively, the phase could be changed in an inner loop. For example, at each power level, for each spot, ultrasound stimulation could be done at each of several different phases. Optionally, once an action potential is observed, the controller moves to the next spot. This procedure produces a map of the minimum power needed to induce an action potential at the most sensitive phase in the cardiac cycle. Alternatively, the power threshold for inducing an action potential is measured for each of several phases at each spot.

In making the map, corrections to the ultrasound power level are optionally made taking into account absorption of ultrasound energy between the transducers and the focused spot. The amount of absorption may be estimated by using known values for absorption lengths of ultrasound at the frequency used, in different types of tissue. Alternatively or additionally, absorption may be measured by using data from the imaging system, if it is an ultrasound imaging system, or by detecting stimulating ultrasound waves reflected back to the transducers. For example, images can be compared at lower ultrasound frequency, where there is less absorption, and higher frequency where there is more absorption, in order to calibrate the amount of absorption at the frequency used for stimulation. In some embodiments of the invention, the ultrasound power flux focused on a given spot in the heart is controlled to within 10%, taking into account errors in the powers and phases of the transducers, and uncertainties in the amount of power that is absorbed between the transducers and the focused spot. Alternatively, the power is controlled only to within 20%, or to within better than 3%.

Corrections are also optionally made to the map by taking into account the finite amplitude of ultrasound at locations other than the focused spot, which can be calculated from the size, spacing, and number of transducers in the array, and by modeling reflections and refraction of ultrasound waves. Such a spatial distribution of the ultrasound intensity could stimulate action potentials first at those other locations, if the tissue there is much more sensitive than the tissue at the focused spot. One way to calculate these corrections is to make a map of sensitivity initially ignoring these effects, and then seeing whether such effects would be important according to that map, and correcting for them, and making a new map. This procedure is repeated until the map changes very little from one iteration to the next. Alternatively or additionally, information about the intensity of ultrasound energy at different locations is obtained by measuring the amplitude of higher harmonics (integer multiples of the transmitted frequency) generated at those locations.

Optionally, data on the induced action potentials from the electrocardiograph, and/or imaging data on the mechanical response to ultrasound stimulation, are used to control the power level of the ultrasound transducers using feedback in real time, instead of or in addition to using this data to make corrections to the applied ultrasound power when analyzing the data afterwards.

Figure 3:
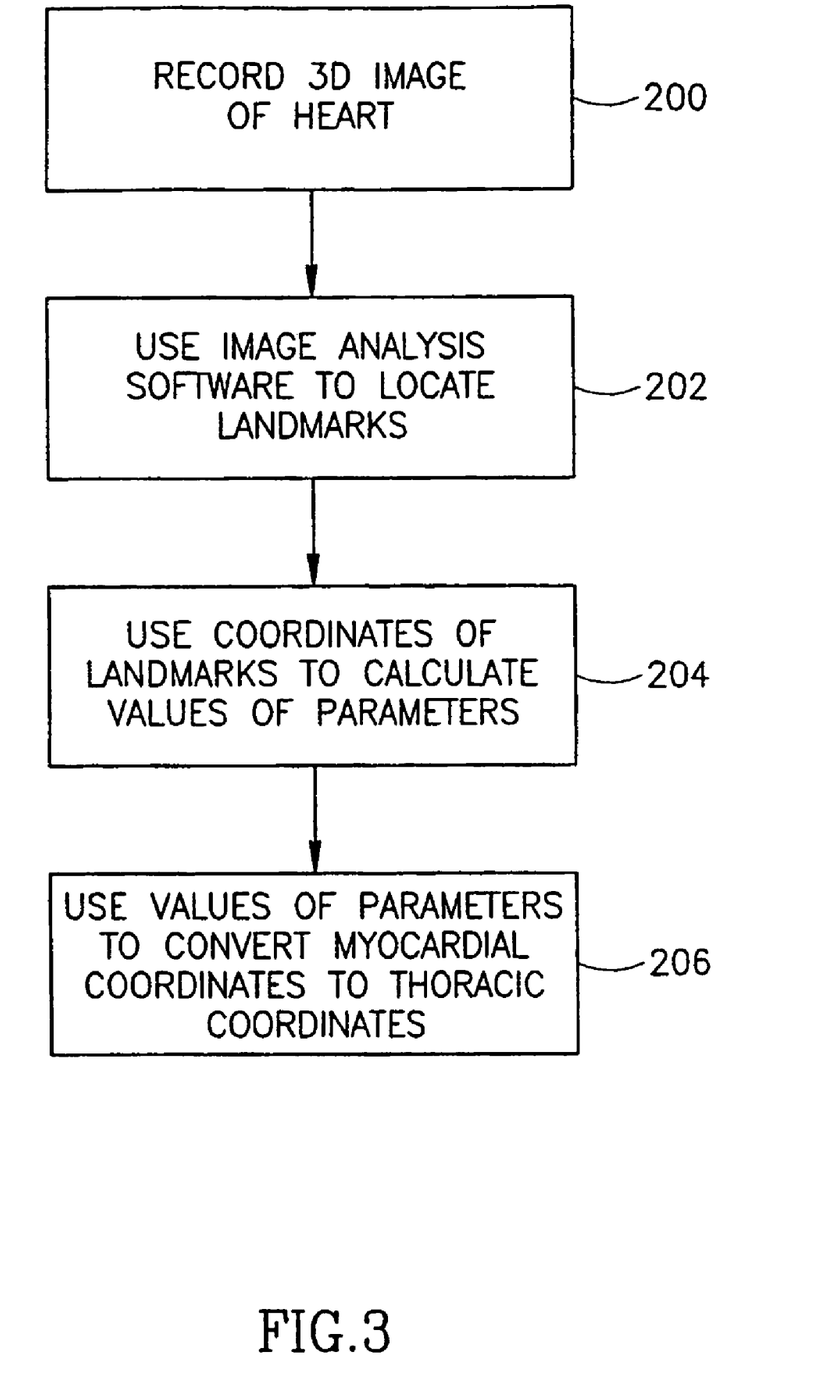
FIG. 3 is a flowchart showing how the imaging system is used to track the location of different spots on the heart in real time.

FIG. 3 is a flowchart showing how the controller analyzes the data from the imaging system and calculates the location (relative to the transducers) of the spot on the heart where the ultrasound energy is to be focused, according to an embodiment of the invention. This is done, for example, using the following steps. At 200, a 3D image of the heart is recorded, using the imaging system. At 202, image analysis software is used to locate in the image key landmarks on the heart, for example the centers of valves, certain branching points of the coronary artery, certain points at the edge of the septum, etc. At 204, the coordinates (relative to the imaging system) of the landmarks are used to calculate the values of a finite set of parameters which substantially characterize the mechanical state of the heart. For example, the parameters comprise three parameters representing the 3D position of the center of the heart, three parameters representing the orientation of the heart in space, and four parameters describing the state of expansion of each chamber of the heart. At 206, the values of the parameters are used to calculate the thoracic coordinates of the desired spot, whose location is defined in myocardial coordinates, according to a algorithm worked out in advance. The algorithm is based on a mathematical model of where each point on the heart is located as a function of the different parameters, for example the state of expansion of each chamber. This coordinate transformation algorithm can be verified for human hearts in general, and perhaps some free parameters are calibrated for individual patients. This verification and calibration is done by locating spots on the heart (other than the landmarks) on the image, and seeing whether their location is correctly predicted by the algorithm.

Other procedures may be used to accomplish the same result. For example, instead of only locating a small set of landmarks on the image, the image processing software determines the location (relative to the imaging system) of each point in a 3D grid of points defined in myocardial coordinates, and interpolation is then used to find the location of the spot. In effect this procedure would use a much larger set of parameters, but a much simpler coordinate conversion algorithm, than the procedure outlined above.

Once the coordinates of the spot are known, the controller calculates the ultrasound wave phases and amplitudes of the transducers in the array required to direct the ultrasound energy to the spot.

Once a map has been made of the sensitivity of the cardiac tissue to stimulation, or of other properties such as delay time of action potentials or refractory time, the information is optionally used to develop and optimize sequences of cardiac stimulation for pacemaking. Selected spatial and temporal sequences of stimulation are tested or modeled, using ultrasound pulses focused on the desired locations, at the desired times in the cardiac cycle, as determined by the electrocardiograph. Optionally, more than one location is stimulated at nearly the same instant. Optionally, the electrocardiograph, and/or the imaging system, is used to measure the strength and regularity of the heartbeat, to assess the efficacy of a given sequence for pacemaking, and the sequence is compared to other sequences. Additionally or alternatively, one or more other indices are used to evaluate a given sequence, including, for example, systolic pressure, systolic left ventricular volume, diastolic left ventricular volume, and/or ejection fraction. (These indices are optionally measured by any conventional means, including the use of images or other data from the ultrasonic, or other, imaging system. Optionally, image analysis is used to calculate one or more of these indices from the images. Alternatively or additionally, the indices are determined by a person viewing the images.) Once an effective sequence is found, a pacemaker using direct electrical stimulation can be programmed and implanted to produce the most effective stimulation sequence.

Figure 4:
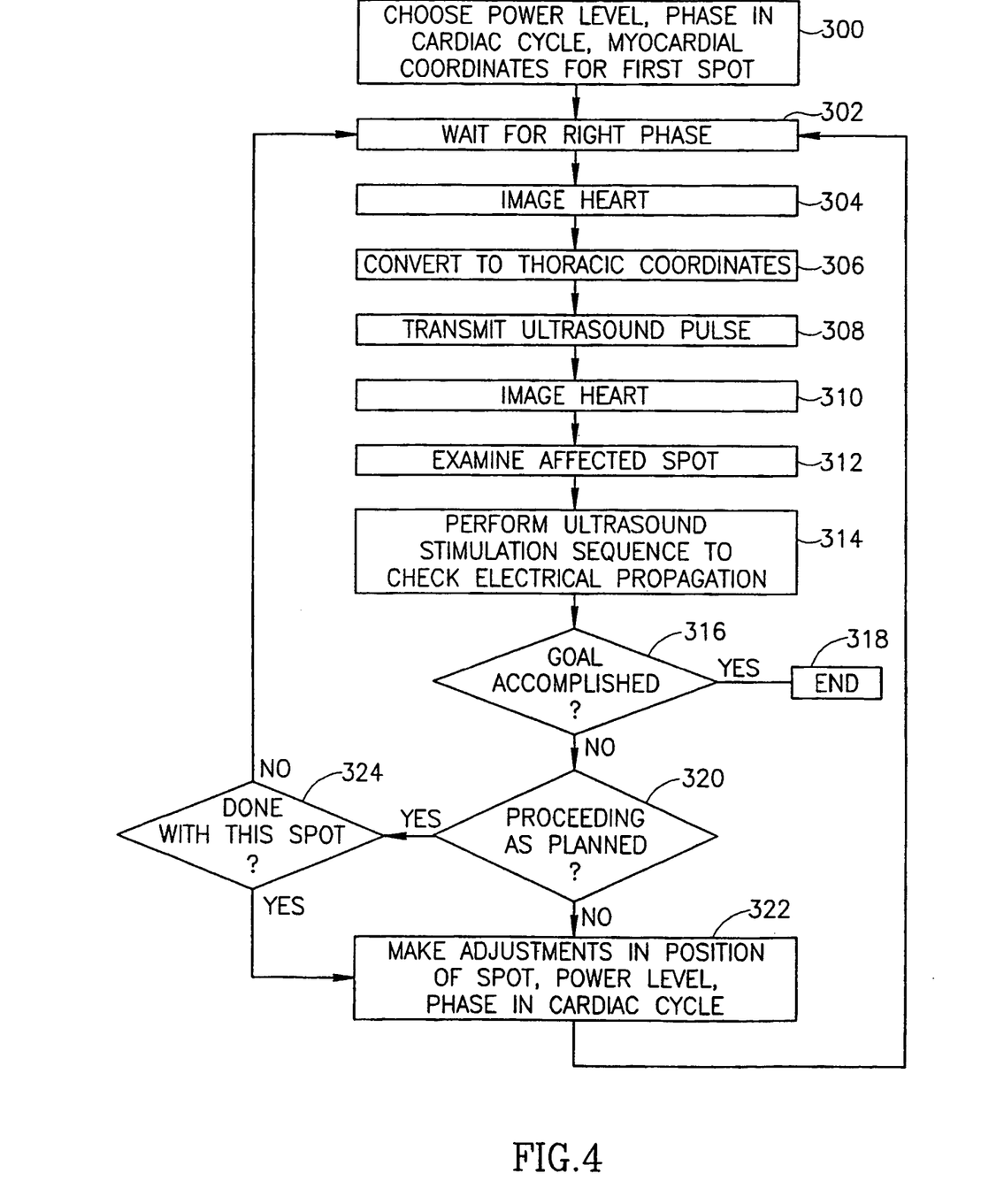
FIG. 4 is a flowchart showing how cardiac tissue is destroyed, while the effects are monitored.

The ultrasound system used for stimulating cardiac tissue can also be used to destroy cardiac tissue, for example diseased or arrhythmogenic tissue. FIG. 4 is a flowchart showing the procedure by which tissue is destroyed, according to an exemplary embodiment of the invention. Initially, at 300, the ultrasound power level, coordinates of the first spot, and phase in the cardiac cycle are chosen. Although it is possible to track the spot continuously as the heart beats, and to keep ultrasound focused on it throughout the cardiac cycle, there are advantages to applying ultrasound power for a time short compared to the cardiac period, and to repeat this at the same phase of the cardiac cycle over several heartbeats if necessary. One advantage is that there may be less error in aiming the ultrasound, since the location of the spot relative to the chest does not vary by that much from one cardiac cycle to the next, at the same phase. Another advantage is that the ultrasound power can be applied to the spot at a phase in the cardiac cycle when the surrounding cardiac tissue is not sensitive to stimulation by ultrasound. In 302, the controller waits for the right phase in the cardiac cycle. Then (304) the heart is imaged, and, as outlined in FIG. 3, the image is used to convert the myocardial coordinates of the chosen spot to thoracic coordinates (306). In 308 a pulse of ultrasound energy is transmitted. The power and duration of the pulse are optionally chosen so that it destroys a small amount of tissue, but not enough to do serious damage to the heart if the energy was not focused in exactly the right spot. In 310, the heart is imaged again, and the image is examined (312) to verify the destruction of tissue at the intended spot. In addition (314), an ultrasound stimulation sequence is optionally performed to verify that the destruction of tissue at that spot has the expected effect on electrical propagation paths. One well known reason for destroying cardiac tissue, possibly even healthy tissue, is to prevent propagation of action potentials on undesired paths. If the imaging and stimulation test reveal that the goal was accomplished (316), the procedure ends (318). If the imaging and/or stimulation test reveal that the ultrasound energy was not aimed correctly (320), or if the power was too high or too low, then appropriate adjustments are made (322), and the procedure returns to 302 to prepare for transmitting another pulse of ultrasound. If the imaging and/or stimulation test reveal that everything is proceeding as planned (320), but that more tissue needs to be destroyed at the same spot (324), then the procedure also returns to 302. If the procedure is proceeding as planned but the work on that spot is done, then the next spot is chosen, and the power level may be adjusted (322), and the procedure returns to 302.

Optionally, tissue is destroyed by heating it, which can kill it or cause it to disintegrate. Alternatively or additionally, tissue is killed by cavitation induced by ultrasound. In either case, the tissue is killed directly, for example by ablating it, or indirectly, for example by inducing apoptosis. Optionally, ultrasound contrast agent is used to increase cavitation effects and/or energy absorption at the site of tissue being killed.

Instead of or in addition to using ultrasound energy from external transducers to kill cardiac tissue, ultrasound stimulation can be used to monitor the killing of cardiac tissue by other means known to the art, such as laser light, radio waves, or ultrasound waves brought to the heart by a cardiac catheter. The words "kill" and "destroy" and their conjugates, as used herein, mean "kill directly or indirectly," and includes, for example, ablation and inducing apoptosis.

The words "locations on the heart" as used herein mean locations on the surface of the heart or inside the heart, including within the myocardium. The terms "position" and "orientation" when used herein with reference to an imaging system, mean position and orientation of the elements of the imaging system whose position and orientation affect the point of view of the images produced by the imaging system. The terms "data analyzer" and "image analyzer" as used herein mean any device which analyzes data, including software running on a general purpose computer, and specially designed digital or analog electronic circuits, whether or not it analyzes data in real time, and whether or not it is located in the vicinity or located remotely. The term "analysis results" produced by a data analyzer from a data set can include a selection of any or all unchanged pieces of data in the data set, as well as the results of mathematical calculations using the pieces of data in the data set. The words "comprise" and "include" and their conjugates as used herein mean "include but are not necessarily limited to." While the invention has been described with reference to certain exemplary embodiments, various modifications will be readily apparent to and may be readily accomplished by persons skilled in the art without departing from the spirit and scope of the above teachings.

The invention claimed is:

1. An ultrasound cardiac stimulation system comprising:
    a spatially selective ultrasound source comprising at least one ultrasound transducer located outside a circulatory system of a body; and
    a controller;
    wherein the controller generates an electrical response in a heart by directing the ultrasound source to transmit a pulse or pulses of ultrasound to one or more locations in the heart on a periodic basis suitable for cardiac pacing, wherein said of ultrasound pulse or pulses are configured to include a rower level and duration suitable to induce an action potential in the heart.

2. A system according to claim 1 and including an injector which injects cardiac drugs into the bloodstream, wherein the controller changes a rate at which cardiac tissue absorbs the drugs by directing the ultrasound source to transmit a high enough power level of ultrasound to one or more locations in the heart.

3. A system according to claim 1, wherein the controller is operative to choose the ultrasound power level.

4. A system according to claim 3, wherein the system has sufficient precision to control the ultrasound power level supplied to cardiac tissue to within ±10%.

5. A system according to claim 4, wherein the system has sufficient precision to control the ultrasound power level supplied to cardiac tissue to within ±3%.

6. A system according to claim 3, and including an injector which injects one or both of drugs for treating the heart and contrast agents into the bloodstream.

7. A system according to claim 6 wherein the injector injects drugs into the bloodstream, and the controller is further configured to change the rate at which cardiac tissue absorbs the drugs by directing the ultrasound source to transmit a high enough power level of ultrasound to one or more locations in the heart.

8. A system according to claim 1, wherein the controller is operative to choose the one or more locations to which the ultrasound is transmitted.

9. A system according to claim 8, wherein the controller controls the ultrasound source to direct ultrasound energy to a designated location, and a point of highest power flux density falls within an axial precision of 3 mm of said designated location.

10. A system according to claim 9, wherein the point of highest power flux density remains within the axial precision of the designated location for at least 1 millisecond.

11. A system according to claim 8, wherein the controller controls the ultrasound source to direct ultrasound energy to a designated location, and the point of highest power flux density falls within a transverse precision of 1 mm of said designated location.

12. A system according to claim 11, wherein the point of highest power flux density remains within the transverse precision of the designated location for at least 1 millisecond.

13. A system according to claim 8, wherein the controller additionally controls the ultrasound source to direct a high enough power level of ultrasound to one or more locations in the heart to kill cardiac tissue by heating.

14. A system according to claim 8, wherein the controller additionally controls the ultrasound source to direct a high enough power level of ultrasound to one or more locations in the heart to kill cardiac tissue by cavitation.

15. A system according to claim 1, and including an electrocardiograph which measures the timing of the cardiac cycle.

16. A system according to claim 15, wherein the electrocardiograph is operative to distinguish the electrical response to the ultrasound, originating at any location in the heart, from the electrical response originating one centimeter away from said location.

17. A system according to claim 15, wherein the controller coordinates the timing of the transmission of ultrasound with the cardiac cycle.

18. A system according to claim 17, wherein said controller coordinates said timing with one particular phase in the cardiac cycle.

19. A system according to claim 17, wherein, said controller coordinates said timing with more than one particular phase in the cardiac cycle.

20. A system according to claim 15, and including a cardiac catheter which generates an electrical response in the heart, and a calibration mode of the controller, wherein the controller, when in the calibration mode, calibrates the ultrasound power transmitted to the heart by the ultrasound array, by comparing a physiological response induced by the ultrasound array to a physiological response induced by the catheter.

21. A system according to claim 20 wherein the physiological responses compared by the controller comprise electrical responses.

22. A system according to claim 20, wherein the physiological responses compared by the controller comprise mechanical responses.

23. A system according to claim 20, wherein the cardiac catheter generates an electrical response by direct electric stimulation.

24. A system according to claim 20, wherein the cardiac catheter comprises an internal ultrasound transducer, and the cardiac catheter generates an electrical response by transmitting ultrasound.

25. A system according to claim 20, wherein the cardiac catheter kills cardiac tissue.

26. A system according to claim 25, and including a laser, wherein the cardiac catheter comprises a light guide, and the light guide carries light from the laser, which light kills cardiac tissue.

27. A system according to claim 15, wherein the controller uses feedback from the electrocardiograph to control the ultrasound power level.

28. A system according to claim 15, wherein the controller is operative to make a map of the heart, showing the ultrasound power flux required to generate the electrical response at each of several locations in the heart.

29. A system according to claim 15, wherein the controller is operative to direct the ultrasound source to transmit a first sequence of timed localized pulses of ultrasound energy to the heart, and a second such sequence which differs from the first sequence in one or both of timing and location of the pulses, and the controller is operative to collect a first data set showing the effects of the first sequence on the heart, and a second data set showing the effects of the second sequence on the heart.

30. A system according to claim 29, and including a cardiac imaging system, and an image analyzer which analyzes images produced by the cardiac imaging system for the first sequence and the second sequence, and calculates one or more of a systolic left ventricular volume for the first and second sequence, a diastolic left ventricular volume for the first and second sequence, and an ejection fraction for the first and second sequence.

31. A system according to claim 1, and including a cardiac imaging system which produces images showing the position of one or more locations on the heart.

32. A system according to claim 31, and including sensors which determine the relative position and orientation of the imaging system and the ultrasound source.

33. A system according to claim 31, wherein the imaging system determines the relative position and orientation of the ultrasound source by imaging.

34. A system according to claim 31, wherein the controller coordinates the timing of the imaging system with the timing of the ultrasound source.

35. A system according to claim 31, wherein the imaging system uses ultrasound imaging.

36. A system according to claim 35, wherein the imaging system shares one or more ultrasound transducers with the ultrasound source used to generate the electric response in the heart.

37. A system according to claim 31, and including image processing software which analyzes the images to determine the position of one or more locations on the heart.

38. A system according to claim 37, wherein the image processing software determines the position of one or more locations on the heart in real time during a cardiac cycle.

39. A system according to claim 31 wherein the controller is operative to make a map of the heart, using data from the imaging system, showing the mechanical response of the heart at one or more locations to ultrasound energy transmitted to one or more locations.

40. A system according to claim 31, wherein the controller uses feedback from the imaging system to control the ultrasound power level.

41. A system according to claim 31, wherein said cardiac imaging system is configured to be synchronized with said ultrasound stimulation, in order to detect short-term mechanical response of heart tissue to the ultrasound stimulation.

42. A system according to claim 1, wherein the ultrasound source comprises a phased array of the ultrasound transducers.

43. A system according to claim 1, wherein at least one of the at least one ultrasound transducer is adapted for use on a surface of the body.

44. A system according to claim 43, wherein the at least one ultrasound transducer comprises at least two ultrasound transducers, sized and spaced so as to be placed between ribs of the body, in such a way as to avoid blocking of ultrasound by the ribs.

45. A system according to claim 1, wherein at least one of the at least one ultrasound transducer is adapted for use in an esophagus of the body.

46. A system according to claim 1, wherein the ultrasound source and the controller are operative to direct the ultrasound energy with 90% of the power flux falling within 3 mm transversely of the point of highest power flux density.

47. A system according to claim 46, wherein the ultrasound source and the controller are operative to direct the ultrasound energy with 90% of the power flux falling within 1 mm transversely of the point of highest power flux density.

48. A system according to claim 1, wherein the ultrasound source and the controller are operative to direct the ultrasound energy with the power flux spreading out to 50% of the highest density thereof, within 6 mm axially of the point of highest power flux density.

49. A system according to claim 48, wherein the ultrasound source and the controller are operative to direct the ultrasound energy with the power flux spreading out to 50% of the highest density thereof, within 1.5 mm axially of the point of highest power flux density.

50. A system according to claim 1, wherein the ultrasound source and the controller are operative to direct the ultrasound energy with a power flux density greater than 30 watts per square centimeter at the point of highest power flux density.

51. A system according to claim 50, wherein the ultrasound source and the controller are operative to direct the ultrasound energy with a power flux density greater than 100 watts per square centimeter at the point of highest power flux density.

52. A system according to claim 51, wherein the ultrasound source and the controller are operative to direct the ultrasound energy with a power flux density greater than 300 watts per square centimeter at the point of highest power flux density.

53. A system according to claim 1, wherein the ultrasound source and the controller are operative to direct the ultrasound energy in a pulse lasting less than 10 milliseconds.

54. A system according to claim 53, wherein the ultrasound source and the controller are operative to direct the ultrasound energy in a pulse lasting less than 1 millisecond.

55. A system according to claim 1, wherein the ultrasound source and the controller are operative to direct the ultrasound energy in a pulse lasting for a duration within 10% of a duration for which the controller is directed to direct the energy.

56. A system according to claim 1, wherein the ultrasound source and the controller are operative to direct the ultrasound energy at a frequency greater than 0.5 megahertz and less than 6 megahertz.

57. A system according to claim 45, and further including an imaging system configured to locate the position of the at least one ultrasound transducer relative to the chest cavity in the esophagus.

58. A system according to claim 45, wherein said at least one ultrasound transducer is additionally configured to act as a cardiac imaging system which produces images showing the position of one or more locations on the heart.

59. A system according to claim 1, wherein said controller is configured to determine whether said ultrasound stimulation has induced said action potential beyond the action potential that already existed as part of the natural cardiac cycle of the heart.

60. A system according to claim 59, wherein said controller is configured to determine the exact threshold for the power level of said ultrasound source, whereat said action potential beyond the action potential that already existed as part of the natural cardiac cycle of the heart is induced by said ultrasound stimulation.

61. A system according to claim 60, wherein, if said action potential beyond the action potential that already existed as part of the natural cardiac cycle of the heart has not been induced by said ultrasound stimulation, said controller is configured to raise the power level of said ultrasound source.

62. A system according to claim 60, wherein, if said action potential beyond the action potential that already existed as part of the natural cardiac cycle of the heart has been induced by said ultrasound stimulation, said controller is configured to lower the power level of said ultrasound source.

63. A method of changing a cardiac stimulation sequence for a patient, comprising:
   a) choosing a test sequence of locations in the heart of the patient, and a time in the cardiac cycle to stimulate each location;
   b) stimulating the test sequence of locations at the chosen times in the cardiac cycle, using an ultrasound cardiac stimulation system from outside the heart;
   c) evaluating a change in cardiac synchronization of the patient associated with the test sequence;
   d) choosing a stimulation sequence for a pacemaker, based at least partly on the change in cardiac synchronization that the test sequence produces; and
   e) changing a stimulation sequence of the heart to conform to the chosen stimulation sequence by modifying operation of the pacemaker.

64. A method according to claim 63, wherein using an ultrasound cardiac stimulation system from outside the heart comprises using an ultrasound stimulation system from outside the body.

65. A method according to claim 63, wherein changing a stimulation sequence of the heart comprises installing a pacemaker.

66. A method according to claim 63, wherein changing a stimulation sequence of the heart comprises adjusting a pacemaker to obtain improved cardiac synchronization.

67. A method according to claim 63, wherein (a), (b) and (c) are performed a plurality of times for different test sequences, and choosing an optimal stimulation sequence is based at least partly on the change in a measure of cardiac performance that the different test sequences produce.

68. A method according to claim 67, wherein the measure of cardiac performance comprises cardiac output.

69. A method according to claim 67, wherein evaluating the change in the measure of cardiac performance comprises using systolic pressure measurements.

70. A method according to claim 67, wherein evaluating the change in the measure of cardiac performance comprises using images of a mechanical response of the heart to the stimulation.

71. A method according to claim 67, wherein at least one of the test sequences comprises a plurality of locations with the same chosen time.

72. A method according to claim 63, wherein evaluating the change in cardiac synchronization comprises using electrocardiograph data.

73. A method according to claim 63, wherein, for each chosen location in the heart, said stimulating is performed at chosen times in the cardiac cycle at one particular phase in the cardiac cycle.

74. A method according to claim 63, wherein, for each location in the heart, said stimulating is performed at chosen times in the cardiac cycle at more than one particular phase in the cardiac cycle.

75. A method according to claim 63, wherein said ultrasound cardiac stimulation system is configured to direct an ultrasound source to transmit a high enough power level of ultrasound to induce an action potential in the heart.

* * * * *